(12) United States Patent
Kim et al.

(10) Patent No.: US 7,932,232 B2
(45) Date of Patent: Apr. 26, 2011

(54) COSMETIC COMPOSITION COMPRISING BETA-FRUCTOSYL-L-ASCORBIC ACID FOR SKIN WHITENING

(75) Inventors: Ki Ho Kim, Chungcheongnam-do (KR); Sang Ki Rhee, Seoul (KR); Chul Ho Kim, Daejeon (KR); Kang Il Ko, Chungcheongnam-do (KR); Soo Nam Park, Seoul (KR); Sang Min Lee, Chungcheongam-do (KR)

(73) Assignees: Bioland Ltd., Cheonan-si (KR); Korea Research Institute of Bioscience & Biotechnology, Daejeon (KR)

( * ) Notice: Subject to any disclaimer, the term of this patent is extended or adjusted under 35 U.S.C. 154(b) by 702 days.

(21) Appl. No.: 11/816,740

(22) PCT Filed: Feb. 23, 2005

(86) PCT No.: PCT/KR2005/000503
§ 371 (c)(1), (2), (4) Date: Aug. 21, 2007

(87) PCT Pub. No.: WO2006/090939
PCT Pub. Date: Aug. 31, 2006

(65) Prior Publication Data
US 2008/0261901 A1 Oct. 23, 2008

(51) Int. Cl.
*A61K 31/7034* (2006.01)
(52) U.S. Cl. .................................................. 514/25
(58) Field of Classification Search ............... 514/25
See application file for complete search history.

(56) References Cited

U.S. PATENT DOCUMENTS

| | | |
|---|---|---|
| 5,137,723 A | 8/1992 | Yamamoto et al. |
| 5,468,850 A | 11/1995 | Mandai et al. |
| 5,882,658 A | 3/1999 | Simon et al. |

FOREIGN PATENT DOCUMENTS

| | | |
|---|---|---|
| JP | 58-198498 A | 11/1983 |
| JP | 01-274019 | 10/1989 |
| JP | 53-98954 A | 8/2007 |
| KR | 0158102 | 8/1998 |
| KR | 0162495 | 8/1998 |
| KR | 10-0207958 | 4/1999 |
| WO | WO 03057707 A1 * | 7/2003 |
| WO | WO 2005026183 A1 * | 3/2005 |

OTHER PUBLICATIONS

Shallenberger et al. Food Chemistry, 1983, 12(3), p. 159-165.*
Jang, Ki-Hyo, et al., Levan frustotransferease from Arthrobactor oxydans J17-21 catalyzes the formation of the Di-D-fructose dianhydride IV from Levan, J. Agric. Food Chem. 2003, 51, 2632-2636.
Muto, Norio et al., Formation of a stable ascorbic acid 2-glucoside by specific transglucosylation with rice seed alpha-glucosidase, Agric. Biol. Chem., 54(7), 1697-1703, 1990.
Song, Ki-Bang et al., Charactistics of levan grustotransferase from Arthrobactor ureafaciens K2032 and difructose anhydride IV formation from levan, Enzyme Microbial Technol., 27, 2000, 212-218.
Staudinger, HJ., Role of ascorbic acid in microsomal electron transport and the possible relationship to hydroxylation reactions, Annals N,Y, Acad. Sci., 92, 1961,195-207.
Williams , N.H. at al., Outer-Sphere electron-transfer reactions of ascorbate anions, Aust. J. Chem., 1982, 35, 1133-1144.

* cited by examiner

*Primary Examiner* — Shaojia Anna Jiang
*Assistant Examiner* — Jonathan S Lau
(74) *Attorney, Agent, or Firm* — Hogan Lovells US LLP

(57) ABSTRACT

The present invention is related to novel cosmetic composition comprising beta-fructosyl-L-ascorbic acid derivatives produced by fructose conversion reaction using by ascorbic acidskin whitening cosmetic composition as an cream, skin, lotion, pack and the like.

4 Claims, 1 Drawing Sheet

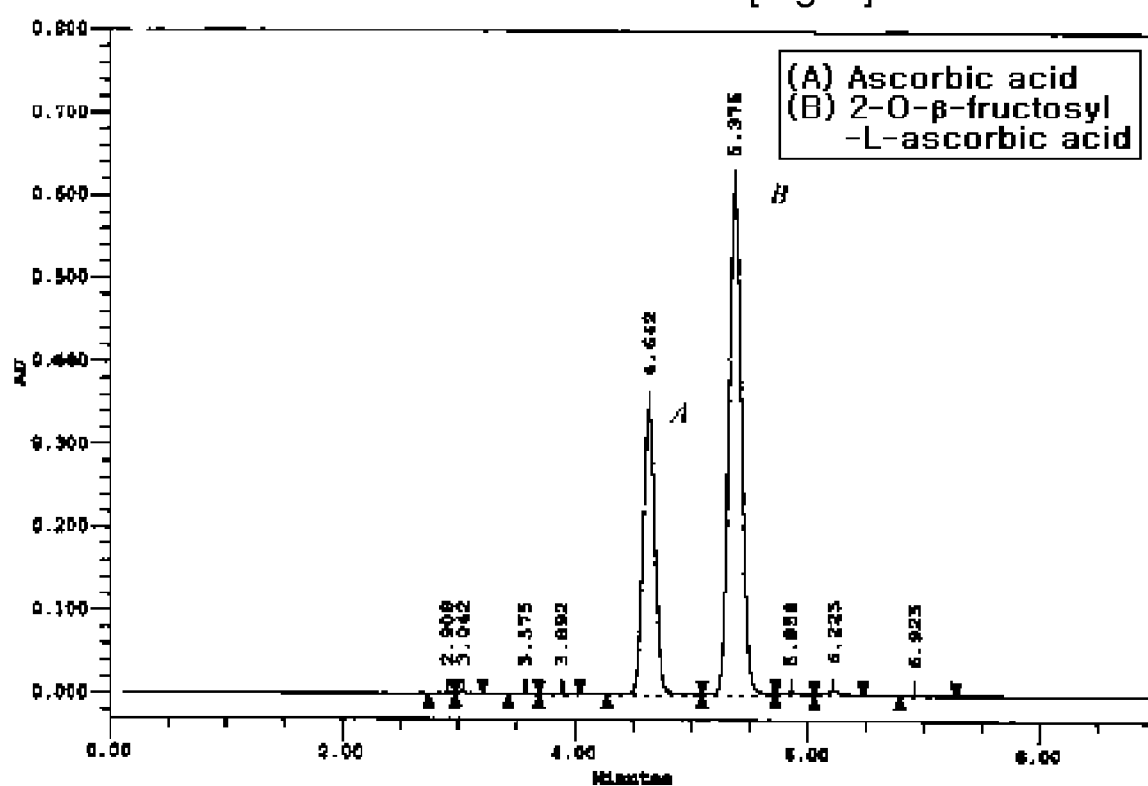

COSMETIC COMPOSITION COMPRISING BETA-FRUCTOSYL-L-ASCORBIC ACID FOR SKIN WHITENING

This application is the U.S. National Phase under 35 U.S.C. §371 of International Application PCT Patent Application No. PCT/KR2005/000503, filed on Feb. 23, 2005, the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention is related to cosmetic composition comprising beta-fructosyl-L-ascorbic acid for skin whitening.

BACKGROUND ART

Skin hyper-pigmentation comes from various origins such as the hormonal disorder followed by the inflammatory response of skin, genetic disease and ultraviolet irradiation, mainly the synthetic disorder and distribution disorder of melanin pigment.

The main function of melanin is scavenging oxygen radical, which can protect skin from the injury. Therefore, it has been known that the plenty of melanin shows potent response on skin system for protecting skin from physical or chemical toxic substance. Melanin is formed by serial steps i.e., converting tyrosine to dopaquinone by tyrosinase enzyme followed by further enzymatic reaction and spontaneous oxidative reaction and so on.

Therefore, the inhibiting methods of melanin biosynthesis for protecting skin tanning are classified by follows: (1) UV protecting method to get rid of the main cause of melanin formation, which is expected to give satisfactory results (2) Inhibiting method of core carbohydrate biosynthesis necessary to tyrosinase activity (3) Inhibiting method of the function of tyrosinase enzyme participating in melanin formation using by kojic acid or arbutin (4) Inhibiting method of cell differentiation using by hydroquinone which has specific toxicity on melanocyte, melanin forming cell, (5) Decolorizing method by reducing melanin formation.

Ascorbic acid, a functional substance showing various physiological activities can be easily decomposed because of its unstable structure and has strong reducing effect since it has endiol group, one double bond group attached to two hydroxyl group within the molecule. It is oxidized to dehydroascorbic acid by the action of ascorbate oxidase enzyme in vivo. The reaction is reversible and it plays a role in maintaining the redox system in vivo, the metabolism of tyrosine, phenylalanine etc. The formation of dark-brown colored melanin from tyrosine is inhibited by ascorbic acid. However, since the ascorbic acid has similar structure to gamma-lactone structure, it is unstable to light, air, water and heat and so on therefore it is easily oxidized to dehydroascorbic acid. In the oxidation reaction of ascorbic acid, ascorbic acid is transformed into dehydroascorbic radical, a oxidizing intermediate, by the action of the dissociation of hydrogen ion, i.e., successive two electronic transition processes and two reactive radicals itself react each other resulting in the formation of one molecule of ascorbic acid and dehydroascorbic acid (Williams, N. H. & Yandell, J. K.; Aust. J. Chem., 35(6) pp 1133-44, 1982).

Antioxidants react with the dehydroascorbate radicals to reduce its leaving group and thereby inhibit the oxidative reaction. The oxidative reaction of ascorbic acid is reversible the oxidized form of dehydroascorbic acid shows vitamin like physiological activities. However, the dehydroascorbic acid is easily hydrolyzed into 2,3-diketo-L-gulonic acid and the acid is more easily dissociated than other general carbonic acid due to two keto group neighboring on carboxyl groups, and thus the formation of lactone having low degree of freedom between atoms is difficult because of its rigidity such as bond angle (120°) of keto group. Accordingly, it is irreversibly dissociated into L-lyxosic acid and L-xylosic acid which has no physiological activities as an ascorbic acid (Staudinger, H., Krisch, K.; Ann. N.Y. Acd. Sci., 92, pp 195, 1961).

Ascorbic acid is very soluble in aqueous solution while sparingly soluble in non-aqueous solution, however it is difficult to be used in medicine, food, cosmetics etc because of its instability to oxidation. There have been previous reports on the synthetic or enzymatic methods to produce modified ascorbate derivatives such as ascorbate sulfate salt, ascorbate phosphate salt, alpha-glycosyl-L-ascorbic acid and so on:

For example, Japanese Patent Publication No. 5,920/83 filed with the inventor's name of Ishio et al and Japanese Patent Publication No. 198,498/83 filed with the inventor's name of Masamoto et al disclose several synthetic methods for preparing alpha-glycosyl-L-ascorbic acid, however the methods have several disadvantages such as low yield, complex mechanism, the difficulty in obtaining the in-toxicity and safety of final products. Accordingly, there have investigated to develop enzymatic method for preparing the glycoside form thereof (glycon type) till now by specific enzyme such as cyclodextrin glucano-transferase and alpha-glucosidase enzyme.

alpha-glucosidase enzyme has been reported to hydrolyze alpha-1,4-linked alpha-glucose units located in terminal ends of dextrin and to have dual functions such as synthesis and hydrolysis of alpha-glycosyl-L-ascorbic acid according to the reaction condition. It has been reported that 2-O— alpha-D-glucopyranosyl-L-ascorbic acid, a glucosylated ascorbic acid, is prepared by using alpha-glucosidase enzyme isolated from mouse intestine (Noris M. et al., Agricultural and Biological Chemistry, 54, pp 1697-1733, 1990) and mixed enzyme, i.e., cyclodextrin glucano-transferase and alpha-glucosidase enzyme (Japanese Patent Nos. 2926412 and 2832848; Korean Patent Registration Nos. 158102 and 162495).

Korean Patent registration No. 207958 invented by the present inventors discloses a method for producing alkyl fructoside using levan sucrase, a sort of fructotransferase enzyme. International Patent Publication No. WO 01/29185 (A1) invented by the present inventors discloses the purification of novel fructotransferase gene from a microbe and the method for producing di-D-fructofuranose-2,6':6,2'dianhydride by transferase activity thereof.

However, there have been no disclosure or suggestion on the novel cosmetic use of beta-fructosyl-L-ascorbic acid derivatives showing improved stability to oxidation and the preparation thereof in above disclosed prior references.

Therefore, the present inventors have endeavored to find chemically stable substance using ascorbic acid as a fructosyl group receptor.

Finally, the present inventors have found that chemically stable beta-fructosyl-L-ascorbic acid derivatives prepared by the method of the present invention have potent inhibiting activity of tyrosinase activity.

DISCLOSURE OF INVENTION

Technical Problem

The present invention provides the cosmetic composition comprising chemically stable and novel beta-fructosyl-L-ascorbic acid derivatives that they have been not produced by chemical and biologic method till now.

Technical Solution

Accordingly, it is an object of the present invention to provide a skin cosmetic composition comprising chemically stable novel beta-fructosyl-L-ascorbic acid derivatives represented by general structural formula (I) produced by fructose transfer reaction using ascorbic acid.

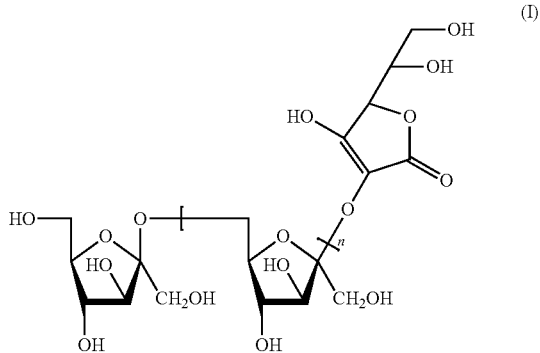

Wherein n is integer of 0 to 10.

Preferable compounds of general structural formula (I) are the compounds wherein n is ranging from 0 to 5 in the present invention. The inventive compounds of the present invention may be prepared in accordance with the following preferred embodiment.

It is another object of the present invention to provide a method for preparing novel beta-fructosyl-L-ascorbic acid derivatives represented by general structural formula (I) comprising the steps consisting of: inoculating fructotransferase-producing microbe into culture medium containing beta-fructosyl sugar compound as a main component, centrifuging the culture medium to remove microbial body, preparing fructose-transferase coenzyme solution by ammonium sulfate precipitation method and subjecting the solution further purification to obtain purified fructotransferase enzyme in step 1; dissolving ascorbic acid in beta-fructosyl sugar compound containing buffer solution, adjusting the pH to 4.5 to 7.0, adding fructotransferase enzyme obtained from above step 1 thereto in dark condition and reacted together to obtain beta-fructosyl-L-ascorbic acid through enzymatic reaction in step 2; subjecting beta-fructosyl-L-ascorbic acid obtained from step 2 to further purification to obtain purified novel beta-fructosyl-L-ascorbic acid derivatives of the present invention.

In the above preparation methods, the above fructotransferase comprises levan fructotransferase, inulin fructotransferase and the mixture thereof.

As a levan fructotransferase-producing microbe described above, the microbes for example, *Arthrobacter oxydans*, *A. ureafacience* and *A. nicotinovorans*, can be preferably used and the microbes for example, *Arthrobacter* oxydans disclosed in the literature (K. H. Jang et al., Journal of Agricultural and Food Chemistry, 51, pp 2632-2636. 2003), *A. ureafacience* disclosed in the literature (K. B. Song et al., Enzyme and Microbial Technology, 27, pp 212-218. 2000) or, *A. nicotinovorans* ATCC 49919 can be more preferably used in the present invention. Besides the microbes, recombinant *E. Coli* transformed with levan fructotransferase gene isolated from *A. ureafacience*, preferably recombinant *E. Coli* (KCTC 8961P) transformed with levan fructotransferase pUDF84 gene isolated from *A. ureafacience*, can be used in the preparation method.

As an inulin fructotransferase-producing microbe described above, the microbes for example, Arthrobacteroxydans, *A. ureafacience*, *A. globiformis* and *Pseudomonas* fluorescence can be preferably used and the microbes for example, *Arthrobacter* oxydans disclosed in the literature (K. H. Jang et al., Journal of Agricultural and Food Chemistry, 51, pp 2632-2636. 2003), *A. globiformis* KCTC 9101 or, *Pseudomonas* fluorescence KCTC 1645 can be more preferably used in the present invention.

As a beta-fructosyl sugar compound described above, levan, inulin or the mixture thereof can be selectively used in the present invention.

In the above described step 1 in the present method, the concentration of levan or inulin used in the microbe inoculation step ranges preferably from 0.01 to 5%, more preferably about 0.5% and it is preferably used by subjecting following steps: dissolving the compound in warm water in the temperature ranging from 50 to 70° C., filtrating with filter having diameter of 0.45 µm and mixing with other culture medium components. It is preferable that the culture is subjected in the temperature ranging from 4 to 80° C., for the period ranging from 3 hours to 5 days, preferably at 30° C., for 24 hours at pH 7.0. Particularly, in case of using recombinant *E. Coli* transformed with levan fructotransferase gene, the fructotransferase of the present invention can be produced by the steps consisting of; inoculating recombinant *E. Coli* into LB medium containing antibiotics, incubation at 37° C., in the speed of 100 to 200 rpm for the period ranging from 8 to 12 hours; inducing the expression of protein by commercially used semi-batch process well known in the art; and isolating and purifying the fructo-transferase coenzyme solution. Additional purifying methods such as dialysis, ion exchange chromatography, gel filtration chromatography etc may be subjected to the fructo-transferase coenzyme solution to obtain more purified fructotransferase enzyme.

In the step 2 described above, levan or inulin can contain buffer solution, preferably, 1 to 20 w % 50 mM phosphate buffer solution, and the ascorbic acid is dissolved in the buffer solution to the extent of concentration ranging from 0.5 to 15 w % and the pH is adjusted in the range of 4.5 to 7.0, preferably 5.0 to 6.0. The reaction with the enzyme is preferably performed in dark condition at the temperature ranging from 25 to 50° C., preferably at 37° C., for the period ranging from 3 hours to 5 days.

In the step 3 described above in the present method, to obtain more purified beta-fructosyl-L-ascorbic acid derivatives, separating methods utilizing the difference of M. W. and electrophilicity between each other, such as solvent extraction, membrane filtration, gel filtration chromatography, column chromatography, HPLC, ion exchange resin chromatography method or the combination method thereof can be adopted selectively, which can isolate beta-fructosyl-L-ascorbic acid derivatives from other by-products such as ascorbic acid, fructose or remaining reaction by-products.

Specifically, the reaction mixture can be isolated by adding appropriate amount of organic solvent thereto and filtrating insoluble substance or by treating active carbon to remove protein substance and staining agent. In an alternative embodiment, de-salting separation method using cation exchange resin and subsequent re-salting separation method using anion exchange resin can be used as purification methods. To purify further, other purification methods such as column chromatography such as silica gel or LiChroprep RP-18 filler could be adopted in the present invention.

The novel beta-fructosyl-L-ascorbic acid derivatives represented by general structural formula (I) produced by fructose transfer reaction from ascorbic acid shows potent inhibiting activity of tyrosinase enzymes, therefore, it can be used as a skin whitening cosmetic composition with the stability as well as other physiological effects such as antioxidant effect or whitening effect.

Hereinafter, the following formulation methods and excipients are merely exemplary and in no way limit the invention.

It is preferable that the present cosmetic composition contains 0.001-20%, more preferably, 0.01-10% by the weight of the inventive composition based on the total weight of the composition. The other components may be a mixture of the ingredients of a conventional cosmetic composition well known in the art.

Cosmetic formulations containing above composition may be prepared in any form such as astringent, nutrient lotion, nutrient cream, massage cream, essence, pack, foundation, cleansing water, soap, treatment, beauty solution and the like.

The cosmetic composition of the present invention can comprises additional additives selected from the group consisting of water soluble vitamin, lipid soluble vitamin, peptide polymer, polysaccharide polymer, sphingolipid and seaweed extract.

Preferable water soluble vitamins are any one which can be mixed with cosmetic, however, various vitamin such as vitamin B1, B2, B6, pyridoxine, pyridoxine HCl, vitamin B12, pantothenic acid, nicotinic acid, nicotinamide, folic acid, vitamin C, vitamin H etc, the salt thereof such as thiamin HCl salt, ascorbic acid Na salt etc or their derivatives such as ascorbic acid-2-phosphonic acid Na salt, ascorbic acid-2-phosphonic acid Mg salt are preferable and those can be obtained by conventional method such as microbial conversion method, purification method from the microbial cultivates, enzymatic method or chemical synthetic method.

Preferable lipid soluble vitamins are any one which can be mixed with cosmetic, however, various vitamin such as vitamin A, $D_2$, $D_3$, E (dl-alpha-tocopherol, d-alpha-tocopherol, d-delta-tocopherol) and their derivatives such as palmitic acid ascorbate, stearic acid ascorbate, dipalmitic acid ascorbate, acetic acid-dl-alpha-tocopherol, nicotinic acid dl-alpha-tocopherol vitamin E, dl-pantothenyl alcohol, D-pantothenyl alcohol, pantothenyl ethylether etc. including the lipid soluble vitamin used in examples of present invention are preferable and those can be obtained by conventional method such as microbial conversion method, purification method from the microbial cultivates, enzymatic method or chemical synthetic method.

Preferable peptide polymers are any one which can be mixed with cosmetic, however, collagen, hydrolysable collagen, gelatin, elastin, hydrolysable gelatin, keratin etc. including the peptide polymer used in examples of present invention are preferable.

Preferable polysaccharide polymers are any one which can be mixed with cosmetic, however, hydroxy ethyl cellulose, xanthin gum, hyaluronic acid Na, chondroitin sulfate or their salt (Na salt etc) and the like are preferable. For example, chondroitin sulfate or the salt thereof etc can be used by being purified from mammal or fishes ordinarily.

Preferable sphingolipid are any one which can be mixed with cosmetic, however, ceramide, pit-sphingosin, sphingolipopolysaccharide and the like are preferable. Sphingo-lipid can be obtained by being purified from mammal, fish, shellfish, yeast or plant etc in conventional method.

Preferable seaweed extract is any one which can be mixed with cosmetic, however, the extract of brown algae, red algae, green algae and the like or the purified carrageenan, alginic acid, arginic acid Na, K isolated therefrom are preferable. Algae extract can be obtained by being purified from seaweed in conventional method. The cosmetic composition of the present invention may combine with other ingredients used in conventional cosmetic composition, if necessary, together with above described essential ingredient.

Preferable above described other ingredients may comprise oil ingredient, humectants, emollients, surfactants, organic or inorganic dye, organic powder, ultraviolet ray absorbing agent, preservatives, antiseptics, antioxidants, plant extract, pH controller, alcohol, pigments, perfumes, refrigerants, blood circulator, antihidrotic, distilled water etc.

Preferable oil ingredients may comprise ester oil, hydrocarbon oil, silicone oil, fluoride oil, animal oil, plant oil and so on.

Preferable ester oil described above may comprise glyceryl tri-2-ethyl hexanoic acid, cetyl 2-ethyl hexanoic acid, isopropyl myristic acid, butyl myristic acid, isopropyl palmitic acid, ethyl stearic acid, octyl palmitic acid, isocetyl isostearic acid, butyl stearic acid, ethyl linoleic acid, isopropyl linoleic acid, ethyl oleic acid, isocetyl myristic acid, isostearyl myristic acid, isostearyl palmitic acid, octyldodecyl myristic acid, isocetyl isostearic acid, diethyl sebasic acid, isopropyl adipic acid, isoalkyl neopetanoic acid, glyceryl tri(capryl, capric acid), trimethylopropane tri-2-ethyl hexanoic acid, trimethylopropane triisostearic acid, pentaerythritol tetra-2 ethyl hexanoic acid, cetyl caprylic acid, decyl lauric acid, hexyl lauric acid, decyl myristic acid, myristyl myristic acid, cetyl myristic acid, stearyl stearic acid, decyl oleic acid, cetyl licinoleic acid, isostearyl lauric acid, isotridecyl myristic acid, isocetyl palmitic acid, octyl stearic acid, isocetyl stearic acid, isodecyl oleic acid, octyldodecyl oleic acid, octyldodecyl linoleic acid, isopropyl isostearic acid, cetostearyl 2-ethyl hexanoic acid, stearyl 2-ethyl hexanoic acid, hexyl isostearic acid, ethylene glycol dioctanoic acid, ethylene glycol dioleic acid, propylene glycol dicapric acid, propylene glycol di(capryl, capric acid), propylene glycol dicaprylic acid, neopentylglycol dicapric acid, neopentylglycol dioctanoic acid, glyceryl tricaprylic acid, glyceryl triundecylic acid, glyceryl triisopalmitic acid, glyceryl triisostearic acid, octyldodecyl neopentanoic acid, isostearyl octanoic acid, octyl isononanoic acid, hexyldecyl neodecanoic acid, octyldodecyl neodecanoic acid, isocetyl isostearic acid, isostearyl isostearic acid, octyldecyl isostearic acid, polyglycerin oleanoic acid ester, polyglycerin isostearic acid ester, triisocetyl citric acid, triisoalkyl citric acid, triisooctyl citric acid, lauryl lactic acid, myristyl lactic acid, cetyl lactic acid, octyldecyl lactic acid, triethyl citric acid, acetyltriethyl citric acid, acetyl tributyl citric acid, trioctyl citric acid, diisostearyl maleic acid, di 2-ethylhexyl hydroxy stearic acid, 2-ethyl hexyl succinic acid, diisobutyl adipic acid, diisopropyl sebasinic acid, dioctyl sebacinic acid, cholesteryl stearic acid, cholesteryl isostearic acid, cholesteryl hydroxy stearic acid, cholesteryl hydroxy stearic acid, cholesteryl oleic acid, dihydrocholesteryl oleic acid, pitsteryl isostearic acid, pitsteryl oleic acid, isocetyl 12-stealoyl hydroxy stearic acid, stearyl 12-stealoyl hydroxy stearic acid, isostearyl 12-stealoyl hydroxy stearic acid. Preferable hydrocarbon oil described above may comprise squalene, liquid paraffin, alpha-olefin oligomer, isoparaffin, ceresin, paraffin, liquid isoparaffin, polybuden, microcrystalline wax, Vaseline and the like.

Preferable silicone oil may comprise polymethylsilicone, methylphenylsilicone, methylcyclopolysiloxane, octamethylpolysiloxane, decamethylpolysiloxane, dodecamethylcyclosiloxane, dimethyl siloxane-methyl cetyloxysiloxan copolymer, dimethyl siloxane-methyl stealoxysiloxane copolymer, alkyl modified silicone oil, amino modified silicone oil and the like.

Preferable fluoride oil can comprise perfluoropolyether and the like.

Preferable animal or plant oil can comprise avocado oil, almond oil, olive oil, sesame oil, rice husk oil, safflower oil, soy-bean oil, corn oil, rape oil, amygdalin oil, palm kernel oil, palm oil, pimaja oil, sunflower oil, fruite seed oil, cotton seed oil, coconut palm oil cucui nut oil, wheat embryo bud oil, rice embryo bud oil, sia butter, evening-primrose oil, marker daymia nut oil, medo home oil, egg yolk oil, lanolin, hempseed oil, mink oil, orange ruppy oil, hohoba oil, carnawa wax, liquid lanolin, solid pimaja wax and the like.

Preferable humectants can comprise water-soluble low molecular humectants, lipophilic low molecular humectants, water-soluble polymer and lipid soluble polymer.

Specifically, preferable water soluble low molecular humectants can comprise cerin, glutamine, sorbitol, mannitol, pyrrolidone-carboxylic acid Na, glycerin, propylene glycol, 1,3-butylene glycol, ethylene glycol, polyethylene glycol (polymerization index. >2), polypropylene glycol (polymerization index >2), lactic acid, lactate salt and the like.

Preferable lipid soluble low molecular humectants can comprise cholesterol, cholesteryl ester and the like.

Preferable water soluble polymer can comprise carboxy vinyl polymer, poly asparaginic acid salt, tragacanth, xanthin gum, HMC(hydroxy methyl celluose), HEC(hydroxy ethyl celluose), HPC(hydroxy propyl celluose), carboxymethylcellulose, water soluble chitin, chitosan, dextrin and the like.

Preferable lipid soluble polymer can comprise polyvinylpyrrolidone-eicocene copolymer, polyvinylpyrrolidone-hexadecene copolymer, nitrocellulose, dextrin fatty acid ester, silicone polymer and the like.

Preferable emollients can comprise long chain acyl glutamic acid cholesteryl ester, cholesteryl hydroxy stearic acid, 12-hydroxy stearic acid, rogic acid, lanolin fatty acid cholesteryl ester and the like.

Preferable surfactant can comprise nonionic surfactants, anionic surfactants, cationic surfactants, ambivalent surfactants and the like.

Specifically, preferable non-ionic surfactants can comprise self-emulsified monostearic acid glycerin, propylene glycol fatty acid ester, glycerin fatty acid ester, polyglycerin fatty acid ester, sorbitan fatty acid ester, polyoxyethylene (POE) sorbitan fatty acid ester, POE sorbitan fatty acid ester, POE glycerin fatty acid ester, POE alkyl ether, POE fatty acid ester, POE solid pimaja oil, POE pimaja oil, POE-POP copolymer, POE-POP alkyl ether, polyether modified silicone, lauric acid alkanol amide, alkyl amine oxide, hydrogen addition soybean phospholipid and the like.

Preferable anionic surfactants can comprise fatty acid soap, alpha-acyl sulfonic acid salt, alkyl sulfonic acid salt, alkyl ally sulfonic acid, alkyl naphthalene sulfonic acid salt, alkyl sulfonic acid salt, POE alkylether sulfate salt, alkyl amide sulfate salt, alkyl phosphate salt, POE alkyl phosphate salt, alkylamide phosphate salt, alkyloylalkyl taurine salt, N-acyl-amino acid salt, POE alkyl ether carboxylic acid salt, alkyl sulfo succinic aid salt, alkyl sulfo-acetic acid salt, acylated hydrolysable collagen peptide salt, perfluoro alkyl phosphate ester and the like.

Preferable cationic surfactant can comprise alkyl trimethyl ammonium chloride, stearyl trimethyl ammonium chloride, stearyl trimethyl ammonium bromide, setostearyltrimethyl ammonium chloride, distearyl dimethyl ammonium chloride, stearyl dimethyl benzyl ammonium chloride, vehenyltrimethyl ammonium bromide, benzalkonium chloride, diethylamino ethyl amide stearic acid, dimethylaminopropyl amide stearic acid, lanolin derivatives quaternary ammonium and the like.

Preferable ambivalent surfactants can comprise carboxy betaine type, amide betaine type, hydroxy sulfo betaine type, phosphobetaine type, aminocarboxylic acid, imidazoline derivatives type, amide amine type and the like.

Preferable organic and inorganic dyes can comprise silicic acid, anhydrous silicic acid, magnesium silicic acid, talc, ceracyte, mica, caolin, bengala, clay, bentonite, titan film mica, oxy chlorine bismuth, zirconium oxide, magnesium oxide, zinc oxide, titan oxide, aluminium oxide, calcium sulfate, barium sulfate, magnesium sulfate, calcium carbonate, magnesium carbonate, ferrous oxide, chromium oxide, chromium hydroxide, calamine, carbon black and the complex thereof as an inorganic dyes; polyamide, polyester, polypropylene, polystyrene, polyurethane, vinyl resin, urea resin, phenol resin, fluoride resin, silicone resin, acryl resin, melamine resin, epoxy resin, polycarbonated resin, divinyl benzene-styrene copolymer, silk powder, cellulose, CI pigment yellow, CI pigment orange as an organic dyes; and their complex etc.

Preferable organic powder can comprise metal soap such as calcium stearate; alkyl phosphonate metal salt such as sodium zinc cetylic acid, zinc laurylic acid, calcium laurylic acid; acylamino acid polyvalent metal salt such as calcium N-lauroyl-b-alanine, zinc N-lauroyl-b-alanine, calcium N-lauroyl-glycine etc.; amide sulfonic acid polyvalent metal salt such as calcium N-lauroyl-taurine, calcium N-palmitoyl-taurine; N-acyl basic amino acid such as N epsilon-lauroyl-L-lysine, N epsilon-palmitoyl-lysine, N alpha-palmitoyl ornitine, N alpha-lauroly arginine, hardened lanolin fatty acid acyl arginine and the like; N-acylpolypeptide such as N-lauroylglycyl glycine; alpha-amino fatty acid such as alpha-amino caprylic acid, alpha-amino lauric acid and the like; polyethylene, polypropylene, nylon, polymethyl-metacrylate, polystyrene, divinylbenzene-styrene copolymer, ethylene tetrafluoride and so on.

Preferable ultraviolet absorbing agents can comprise paraminobenzoic acid, paraamonoethyl benzoate, paramino amyl benzoate, paramino octyl benzoate, ethyleneglycol salicylate, phenyl salicylate, octyl salicylate, benzyl salicylate, butylphenyl salicylate, homomentyl salicylate, benzyl cinnamic acid, paramethoxy 2-ethoxy ethyl cinnamic acid, paramethoxy octyl cinnamic acid, diparamethoxy mono-2-ethylhexane glyceryl cinnamic acid, paramethoxy isopropyl cinnamic acid, di-isopropyl-diisopropyl cinnamate ester mixture, urokanic acid, ethyl urokanic acid, hydroxy methoxy benzophenone, hydroxymethoxy benzophenone sulfonic acid and their salt, dihydroxy methoxy benzophenone, dihydroxy methoxy benzophenone disulfonate Na, dihydroxy benzophenone, tetrahydroxybenzophenone, 4-tert-butyl-4'methoxydibenzoylmethane, 2,4,6-trianilino-p-(carbo-2-ethylhexyl-1'oxy)-1,3,5-triazine, 2-(2-hydroxy-5-methylphenyl) benzotriazole and the like.

Preferable preservatives can comprise hinokitiol, trichloric acid, trichlorohydroxydiphenylether, chlorohexidine glucuronate, phenoxyethanol, resorcine, isopropyl-methylphenol, azulene, salicylic acid, zinc pilithione, bezalconium HCl, photosensitizer 301, mononitroguaiacol Na, undecylenic acid etc.

Preferable antioxidants can comprise butylhydroxyanisole, propyl gallate, ellisorbate and the like.

Preferable pH controller can comprise citric acid, sodium citrate, malic acid, sodium malate, fumaric acid, sodium fumaric acid, succinic acid, sodium succinic acid, sodium hydroxide, sodium hydrogen phosphate and the like.

Preferable alcohol can comprise cetyl alcohol etc.

Furthermore, other ingredient addable to above described component and the amount thereof is not limited within the scope of the purpose and effect of the present invention, however, it is preferable that the amount of the other ingredients ranges from 0.01 to 50%, more preferably, 0.01 to 30% in that of total composition.

The cosmetic composition of the present invention can be modified as a solution, emulsion, cohesive mixture etc.

Above described ingredients such as water-soluble vitamin, lipid soluble vitamin, peptide polymer, polysaccharide polymer, sphingolipid, sea weed extract and addable ingredients which can be added other than above described ingredients if necessary, can be obtained by conventional methods disclosed in the literature (Matsumoto Mithio; Manual for the development of transdermal applied preparation. Seisi Press, 1st Ed., 1985).

Inventive compounds of the present invention have no toxicity and adverse effect therefore, they can be used with safe.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

Advavtageous Effects

As described in the present invention, present invention provides novel cosmetic composition comprising beta-fructosyl-L-ascorbic acid derivatives produced by fructose conversion reaction using by ascorbic acid and the compounds show potent inhibiting effect on the activity of tyrosinase enzyme.

DESCRIPTION OF DRAWINGS

FIG. 1 shows that the retention time of 2-O-beta-fructosyl-L-ascorbic acid is determined by HPLC column chromatography compared with that of L-ascorbic acid.

BEST MODE

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

The following Reference Example, Examples and Experimental Examples are intended to further illustrate the present invention without limiting its scope.

Reference Example 1

The Determination of Levan Fructotransferase Activity

The amount of formed fructose was determined by the step consisting of; mixing 20 μL of enzyme solution with 180 μL of 1% levan solution prepared by using 50 mM phosphate buffer solution (pH 6.5), reacting together at 37° C., for 30 minutes to produce fructose, which is modified method disclosed in the literature (Somogyi M. Notes on sugar determination, J. Biol. Chem., 195, pp 19-23, 1952).

The one unit of enzymatic activity is defined as the amount of enzyme to produce 1 μM of fructose per 1 minute.

Reference Example 2

The Determination of Inulin Fructotransferase Activity

The amount of formed fructose was determined by the step consisting of; mixing 20 μL of enzyme solution with 180 μL of 1% inulin solution prepared by using 50 mM phosphate buffer solution (pH 5.5), reacting together at 45° C., for 30 minutes to produce fructose, which is modified Nelson-Somogyi method.

The one unit of enzymatic activity is defined as the amount of enzyme to produce 1 μM of fructose per 1 minute.

EXAMPLE 1

The Preparation of Fructotransferase 1-1, Levan Fructotransferase

Each selected microbe among *Arthrobacter* genus microbes known to produce Levan fructotransferase enzyme, i.e., *Arthrobacter* oxydans disclosed in the literature (K. H. Jang et al., Journal of Agricultural and Food Chemistry, 51, pp 2632-2636. 2003), *A. ureafacience* K2032 disclosed in the literature (K. B. Song et al., Enzyme and Microbial Technology, 27, pp 212-218. 2000) and *A. nicotinovorans* ATCC 49919, was inoculated into the culture medium containing 0.5% levan (w/v), 0.3% NaNO3, 0.05% MgSO4, 0.02% MnCl2, 0.1% $K_2HPO_4$ and 0.4% yeast extract and incubated at 30° C. for 24 hours. The levan used in the experiment was subjected to pre-treatment, i.e., the levan was dissolved in water, filtered with 0.45 μm of filter paper prior to the mixing step with other components. The culture medium was subjected to centrifugation to remove microbial body and precipitation with ammonium sulfate precipitation method providing with the precipitation of remaining protein from the supernatant to obtain levan fructotransferase coenzyme solution.

The levan fructotransferase coenzymes solution was subjected to dialysis with 20 mM sodium phosphate buffer (pH 6.5), adsorption with Q-sepharose FF anion exchange chromatography column (2.5×500 mm, Pharmacia Co., Piscataway, N.J., USA) stabilized with identical buffer solution (pH 6.5) and elution with NaCl solution using identical buffer solution of which salt concentration had been gradually increased with the speed of 0.45 mL/min starting with 0.5M solution. Eluted levan fructotransferase solution was concentrated with Centriplus (Amicon Co., Beverly, USA) and then subjected to dialysis with identical buffer solution repeatedly. Subsequently, desalted enzymes solution was subjected to adsorption with mono-Q HR 5/5 chromatography stabilized with phosphate buffer solution (Pharmacia Co. USA) and enzyme was eluted with NaCl solution using identical buffer solution of which salt concentration had been gradually increased with the speed of 0.5 mL/min starting with 0.5M solution. Eluted levan fructotransferase solution was concentrated with Centriplus (Amicon Co., Beverly, USA) and then subjected to dialysis with identical buffer solution to obtain purified levan fructotransferase.

Through above purification method, high purified (about ×70 purification degree) and high yield (20-30%) of levan fructotransferase enzyme could be obtained.

1-2. Recombinant levan fructotransferase

Recombinant *E. Coli* transformed with levan fructotransferase gene isolated from *Arthrobacter* ureafacience prepared by the procedure disclosed in Korean Patent Registration No. 380970 was used in mass production of levan fructotransferase enzyme.

The recombinant *E. Coli* was inoculated into 100 mL of LB culture medium added with ampicillin in an amount of 100 mg/L, incubated at 37° C. for 10 hours with a speed of 115 rpm and used as a seeding microbe in following fed-batch culture. The fed-batch culture was performed by cell growth step and enzyme protein producing step to obtain high concentration of cells. The culture medium containing 13.3 g/L KH2PO4, 4.0 g/L yeast extract, 6.0 g/L glucose, 1.7 g/L citric acid, 1.2 g/L MgS04.7H2O, 0.1 g/L thiamine-HCl, 0.14 g/L ampicillin was used as an initial batch type culture medium. At cell growth step, the culture medium containing same composition with those of above described culture medium excluded that the concentration of glucose therein was increased to 700 g/L to minimize the increase of volume and increase cell concentration and NH4OH was used as a nitrogen resource maintaining its pH. At enzyme expression step, IPTG was poured into the culture medium in a concentration of 0.02 mM/L/g cell when the absorbance of culture medium at 600 nm had reached to about 100. Through above described batch culture, final produced amount of levan fructo-transferase expressed by IPTG was about 3 g/L.

1-3. Inulin fructotransferase

Each selected microbe among the microbes known to produce inulin fructo-transferase enzyme, i.e., *Arthrobacter* ureafaciene KCTC 8961P, *A. globiformis* KCTC 9101 and *Pseudomonas* fluorescence KCTC 1645 was inoculated into the culture medium containing 0.5% inulin (w/v), 0.3% NaNO3, 0.05% MgSO4, 0.02% MnCl2, 0.1% K2HPO4 and 0.3% yeast extract and incubated at 30° C. for 24 hours. The inulin used in the experiment was subjected to pre-treatment, i.e., the inulin was dissolved in warm water having a temperature of 60° C., filtered with 0.45 μm of filter paper prior to the mixing step with other components. The culture medium was subjected to centrifugation to remove microbial body and precipitation with ammonium sulfate precipitation method providing with the precipitation of remaining protein from the supernatant to obtain levan fructotransferase coenzyme solution.

The levan fructotransferase coenzymes solution was subjected to dialysis with 20 mM sodium phosphate buffer (pH 6.5), adsorption with Q-sepharose FF anion exchange chromatography column (2.5×500 mm, Pharmacia Co., Piscataway, N.J., USA) stabilized with identical buffer solution (pH 6.5) and elution with NaCl solution using identical buffer solution of which salt concentration had been gradually increased with the speed of 0.45 mL/min starting with 0.5M solution. Eluted inulin fructotransferase solution was concentrated with Centriplus (Amicon Co., Beverly, USA) and then subjected to dialysis with identical buffer solution repeatedly. Subsequently, desalted enzymes solution was subjected to adsorption with mono-Q HR 5/5 chromatography stabilized with phosphate buffer solution (Pharmacia Co. USA) and enzyme was eluted with NaCl solution using identical buffer solution of which salt concentration had been gradually increased with the speed of 0.5 mL/min starting with 0.5M solution. Eluted inulin fructotransferase solution was concentrated with Centriplus (Amicon Co., Beverly, USA) and then subjected to dialysis with identical buffer solution to obtain purified inulin fructotransferase.

Through above purification method, high purified (about ×80 purification degree) and high yield (20-30%) of inulin fructotransferase enzyme could be obtained.

1-4. Ammonium Sulfate Precipitation Method

The fructotransferase producing microbes disclosed in Example 1-1. 1-2 and 1-3 were subjected to mass culture and centrifugation at 4° C. (6000 rpm, 30 mins) to remove microbial body and obtain supernatant. (NH4)2SO4 was dropwise added to the supernatant at 4° C. to be saturated to 80% and left alone for one night. The produced precipitates were collected by centrifugation (600 rpm, 20 mins), dissolved in appropriate amount of 20 mM phosphate buffer solution (pH 6.5) and subjected to dialysis with identical buffer solution sufficiently. The resulting precipitates i.e., inactivated proteins were removed by centrifugation and the supernatant was used as a sample in following ion exchange chromatography.

1-5. Ion Exchange Chromatography

Activated Q-sepharose column (50×2.5 cm) was equilibrated with 20 mM phosphate buffer solution (pH 6.5). The enzyme solution prepared by ammonium sulfate precipitation method was adsorbed therein and then repeated washing procedure consisting of eluting with identical buffer solution and washing to remove non-adsorbed protein and other miscellaneous materials was performed. The protein elution was subjected to elution with increasing the concentration of NaCl solution resulting in linear gradient started from 0 ended to 0.5M with a speed of 0.45 mL/min and fractionation to obtain several fractions in an amount of 6.5 mL/test tube to determine the amount of protein and enzyme activity in each test tube. The collected enzyme fractions obtained from above described ion exchange column chromatography were subjected to dialysis with 20 mM phosphate buffer solution (pH 6.5) and concentrated with Centriplus (Amicon Co., USA) to obtain purified enzyme.

EXAMPLE 2

The preparation of beta-fructosyl-L-ascorbic acid by levan fructo-transferase (1)

4% levan and 1% ascorbic acid were dissolved in 50 mM of phosphate buffer solution (pH 6.0) and the pH of the solution was adjusted to 6.0 using by 4N NaOH. 100 mL of the solution was poured into brown bottle and levan fructotransferase derived from *Arthrobacter* oxydans (50 units/g of levan) was added thereto and sealed up. The solution was stirred at 37° C. for 72 hours to proceed the enzymatic reaction. In HPLC analysis of the reaction product, about 30% ascorbic acid was transformed into ascorbic acid fructoside. The reaction mixture was heated to inactivate unreacted enzyme. The solution was subjected to filtration and resulting supernatant was subjected to decolorization with activated carbon, concentration to obtain purposed beta-fructosyl-L-ascorbic acid with about 90% yield in dry weight base of final product for the starting material.

EXAMPLE 3

The preparation of beta-fructosyl-L-ascorbic acid by levan fructo-transferase (2)

6% levan and 2% ascorbic acid were dissolved in 50 mM of phosphate buffer solution (pH 6.0) and the pH of the solution was adjusted to 6.0 using by 4N NaOH. 100 mL of the solution was poured into brown bottle and levan fructotransferase derived from *Arthrobacter* nicotinovorans (50 units/g of levan) was added thereto and sealed up. The solution was stirred at 37° C. for 72 hours to proceed the enzymatic reaction. In HPLC analysis of the reaction product, about 27% ascorbic acid was transformed to ascorbic acid fructoside. The reaction mixture was heated to inactivate un-reacted enzyme. The solution was subjected to filtration and resulting supernatant was subjected to decolorization with activated carbon, concentration to obtain purposed beta-fructosyl-L-ascorbic acid with about 85% yield in dry weight base of final product for the starting material.

EXAMPLE 4

The Preparation of Beta-Fructosyl-L-Ascorbic Acid by Levan Fructotransferase (3)

4% levan and 2% ascorbic acid were dissolved in 50 mM of phosphate buffer solution (pH 6.0) and the pH of the solution was adjusted to 6.0 using by 4N NaOH. 100 mL of the solution was poured into brown bottle and levan fructotransferase derived from *Arthrobacter* ureafacience (100 units/g of levan) was added thereto and sealed up. The solution was stirred at 37° C. for 72 hours to proceed the enzymatic reaction. In HPLC analysis of the reaction product, about 33% ascorbic acid was transformed to ascorbic acid fructoside. The reaction mixture was heated to inactivate un-reacted enzyme. The solution was subjected to filtration and resulting supernatant was subjected to decolorization with activated carbon, concentration to obtain purposed beta-fructosyl-L-ascorbic acid with about 72% yield in dry weight base of final product for the starting material.

EXAMPLE 5

The Preparation of Beta-Fructosyl-L-Ascorbic Acid by Inulin Fructotransferase (1)

10% inulin and 2% ascorbic acid were dissolved in 50 mM of phosphate buffer solution (pH 5.5) and the pH of the solution was adjusted to 5.5 using by 4N NaOH. 100 mL of the solution was poured into brown bottle and inulin fructotransferase derived from *Arthrobacter* ureafacience (50 units/g of inulin) was added thereto and sealed up. The solution was stirred at 37° C. for 72 hours to proceed the enzymatic reaction. In HPLC analysis of the reaction product, about 27% ascorbic acid was transformed to ascorbic acid fructoside. The reaction mixture was heated to inactivate un-reacted enzyme. The solution was subjected to filtration and resulting supernatant was subjected to decolorization with activated carbon, concentration to obtain purposed beta-fructosyl-L-ascorbic acid with about 91% yield in dry weight base of final product for the starting material.

EXAMPLE 6

The Preparation of Beta-Fructosyl-L-Ascorbic Acid by Inulin Fructotransferase (2)

15% inulin and 3% ascorbic acid were dissolved in 50 mM of phosphate buffer solution (pH 5.5) and the pH of the solution was adjusted to 5.5 using by 4N NaOH. 100 mL of the solution was poured into brown bottle and inulin fructotransferase derived from *Pseudomonas* fluorescence (50 units/g of inulin) was added thereto and sealed up. The solution was stirred at 37° C. for 72 hours to proceed the enzymatic reaction. In HPLC analysis of the reaction product, about 25% ascorbic acid was transformed into ascorbic acid fructoside. The reaction mixture was heated to inactivate un-reacted enzyme. The solution was subjected to filtration and resulting supernatant was subjected to decolorization with activated carbon, concentration to obtain purposed beta-fructosyl-L-ascorbic acid with about 83% yield in dry weight base of final product for the starting material.

EXAMPLE 7

The preparation of beta-fructosyl-L-ascorbic acid by inulin fructo-transferase (3)

10% inulin and 3% ascorbic acid were dissolved in 50 mM of phosphate buffer solution (pH 5.5) and the pH of the solution was adjusted to 5.5 using by 4N NaOH. 100 mL of the solution was poured into brown bottle and inulin fructotransferase derived from *Arthrobacter* globiformis (100 units/g of inulin) was added thereto and sealed up. The solution was stirred at 37° C. for 72 hours to proceed the enzymatic reaction. In HPLC analysis of the reaction product, about 30% ascorbic acid was transformed to ascorbic acid fructoside. The reaction mixture was heated to inactivate un-reacted enzyme. The solution was subjected to filtration and resulting supernatant was subjected to decolorization with activated carbon, concentration to obtain purposed beta-fructosyl-L-ascorbic acid with about 94% yield in dry weight base of final product for the starting material.

EXAMPLE 8

The Preparation of Beta-Fructosyl-L-Ascorbic Acid by Recombinant Levan Fructotransferase (1)

6% levan and 3% ascorbic acid were dissolved in 50 mM of phosphate buffer solution (pH 6.0) and the pH of the solution was adjusted to 6.0 using by 4N NaOH. 100 mL of the solution was poured into 5L enzyme reactor equipped with temperature and pH controller and mixing apparatus and the reactor was shielded with aluminum foil to shade the light. The recombinant levan fructotransferase derived from *Arthrobacter* ureafacience (200 units/g of levan) was added thereto and sealed up. The solution was reacted with stirring at 37° C. for 72 hours in the speed of 100 rpm (pH 6.5) to proceed the fructose conversion enzymatic reaction. In the HPLC analysis of the reaction product, about 35% ascorbic acid was transformed to ascorbic acid fructoside. The reaction mixture was heated to inactivate un-reacted enzyme. The solution was subjected to filtration and resulting supernatant was subjected to de-colorization with activated carbon, concentration to obtain purposed beta-fructosyl-L-asorbic acid with about 88% yield in dry weight base of final product for the starting material.

EXAMPLE 9

The purification of 2-O-beta-fructosyl-L-ascorbic acid

To purify 2-O-beta-fructosyl-L-ascorbic acid from the reaction mixtures prepared from Examples 2 to 8, following procedure was performed. 100 mL of the reaction mixture was precipitated with alcohol. The precipitates were removed and the supernatant was dried in vacuo. The dried solid was dissolved in distilled water and the pH of the solution was adjusted to 3.0 with diluted HCl. The solution was subjected to column chromatography filled with LiChroprep RP-18 column and eluting with distilled water. Resulting elutes were evaporated to leave pure 2-O-beta-fructosyl-L-ascorbic acid (about 80% yield).

$^1$H-NMR (D2O, 250 MHz) delta 3.50-4.20 (m, 5H), 3.73 (dd, J=14, 4 Hz, 2H), 3.93 (dd, J=12.0, 2.0 Hz, 1H), 4.81 (m, 3H);

13C-NMR (D2O, 62.5 MHz) delta 51.2, 57.7, 60.2, 60.4, 61.6, 67.3, 70.7, 74.6, 75.7, 116.2, 153.7, 171.8;

HPLC analysis: the retention time of 2-O-beta-fructosyl-L-ascorbic acid was determined by HPLC column chromatography having following condition compared with that of L-ascorbic acid: (See FIG. 1)

Column; Capcell Pak C18, (4.6×250 mm, Sheido Co.)
Mobile phase; 0.05 M KH2PO4 (pH 2.2 adjusted with phosphoric acid)
Flow rate; 1.0 mL/min
Detector; UV lambda=254 nm (Photodiode detector 996, waters)
Injection volume; 20 µL
Retention time of 2-O-beta-fructosyl-L-ascorbic acid; 5.37 min
Retention time of L-ascorbic acid; 4.64 min Experimental Example 1

Fructose Transfer Enzyme Reaction by Levan Fructotransferase

In order to determine the conversion rate of each enzymes from ascorbic acid to ascorbic acid fructoside, the experiment was performed as follows.

4% levan and 1% ascorbic acid were dissolved in 50 mM of phosphate buffer solution (pH 6.0) and the pH of the solution was adjusted to 6.0 using by 4N NaOH. 100 mL of the solution was poured into three light-shielded brown bottles and the levan fructotransferase enzymes derived from various microbes prepared from Example 1 (10 units/g of levan) was added thereto and sealed up. The solution was stirred at 37° C. for 48 hours to proceed the enzyme reaction. After the reaction, the reaction product was stored at −20° C. and it is confirmed that ascorbic acid was converted into ascorbic acid fructoside by HPLC analysis, At the result, the conversion rates of each enzyme derived from *Arthrobacter oxydans*, *Arthrobacter nicotinovorans* and *Arthrobacter* ureafacience were 28%, 25% and 35% respectively.

Experimental Example 2

Fructose Transfer Enzyme Reaction by Inulin Fructotransferase

In order to determine the conversion rates of each enzymes from ascorbic acid to ascorbic acid fructoside, the experiment was performed as follows.

4% inulin and 3% ascorbic acid were dissolved in 50 mM of phosphate buffer solution (pH 5.5) and the pH of the solution was adjusted to 5.5 using by 4N NaOH. 100 mL of the solution was poured into three light-shielded brown bottles and the inulin fructotransferase enzymes derived from various microbes prepared from Example 2 (10 units/g of inulin) was added thereto and sealed up. The solution was stirred at 37° C. for 48 hours to proceed the enzyme reaction. After the reaction, the reaction product was stored at −20° C. and it is confirmed that ascorbic acid was converted into ascorbic acid fructoside by HPLC analysis, At the result, the conversion rates of each enzyme derived from *Arthrobacter ureafacience*, *Arthrobacter globiformis* and *Pseudomonas fluorescence* were 23%, 26% and 20% respectively.

Experimental Example 3

Tyrosinase Activity Inhibition Assay

In order to confirm the inhibition effect of the 2-O-beta-fructosyl-L-ascorbic acid prepared in Example 9 on tyrosinase enzyme, the experiment was performed by following procedure.

The mixture consisting of 0.3 mg/mL of L-tyrosine (Sigma Co. Ltd), 1.0 mL of 0.1M potassium buffer solution (pH 6.8) and 0.9 mL of various concentrations of 2-O-beta-fructosyl-L-ascorbic acid, i.e., 1, 5, 50, 100, 250, 500 ug/mL was incubated at 37° C., for 10 to 20 mins. 0.1 mL of tyrosinase enzyme (1250 units/mL, Sigma Co. Ltd) was added thereto and further incubated for 10 mins. The solution was stopped by dipping into ice water.

As a positive control and negative control groups, L-ascorbic acid and potassium buffer solution were subjected to identical procedure with above described procedure to compare the inhibiting effect on the activity of tyrosinase enzyme. The absorbance was measured at 475 nm by UV spectrophotometer (Hewlett-Packard Co. Ltd, G1103A) and the inhibitory activity of tyrosinase enzymes was calculated by following equation 1.

$$\text{Inhibition}(\%) = [1 - (A/B)] \times 100 \qquad \text{[equation 1]}$$

Where, A is the enzyme activity of test group and B is the enzyme activity of control group.

As the result, the $IC_{50}$ of 2-O-beta-fructosyl-L-ascorbic (Mw 319) acid and L-ascorbic acid (Mw 176) showed 120.1 and 63.21 ug/mL respectively, therefore, the novel beta-fructosyl-L-ascorbic acid produced by present invention have inhibition considering their molecular weights.

Hereinafter, the formulating methods and kinds of excipients will be described, but the present invention is not limited to them. The representative preparation examples were described as follows.

Preparation Example 1

Bath Solution 21 wt. % of DL-sodium lactate, 8 wt. % of sodium pyruvic acid, 5 wt. % of 2-O-beta-fructosyl-L-ascorbic acid, 40 wt. % of ethanol, 26 wt. % of distilled water and appropriate amount of dye and flavoring agents were mixed to make bath solution according to conventional lotion preparation method.

It is appropriate to use the bath solution by diluting with 100-10,000 fold washing water for use as a skin beauty and skin whitening agent. Cleansing water, astringent and moisturizing solution could be used instead of washing water described above.

Preparation Example 2

Skin Lotion 3 wt. % of glycerin, 2 wt. % of butylene glycol, 2 wt. % of propylene glycol and appropriate amount of preservative were poured into distilled water and mixed to be dissolved completely. 1 wt. % of POE (60) Hardening Glycerin oil heated at 37° C. to be dissolved and flavoring agent were poured to 80.9 wt. % of distilled water. 1 wt. % of 2-O-beta-fructosyl-L-ascorbic acid, 10 wt. % of ethanol, 0.1 wt. % of triethanolamine and miscellaneous dye were mixed thereto and stirred sufficiently to obtain purposed skin lotion.

Preparation Example 3

Milk Lotion 1.7 wt. % of sitosterol, 1.5 wt. % of polyglyceryl 2-olate, 0.7 wt. % of ceramide, 1.2 wt. % of cetares-4 and 1.5 wt. % of cholesterol were mixed and homogenized. The mixture of 1 wt. % of 2-O-beta-fructosyl-L-ascorbic acid, 0.4 wt. % of dicetylphosphate, 5.0 wt. % of conc-glycerin, 10 wt. % of sunflower oil, 0.2 wt. % of carboxyvinylpolymer, 0.3 wt. % of xantan gum and preservatives was dissolved by heating in accordance with well-known procedure in the art. 76.5 wt % of distilled water was added thereto and emulsified by Homo-mixer. Appropriate amount of flavoring agent was added thereto, mixed to obtain purposed milk lotion. The lotion can be used as a sun block, skin beauty and skin whitening agent with high quality.

Preparation Example 4

Nutrient Cream 4 wt. % of sitosterol, 3 wt. % of polyglyceryl 2-olate, 0.7 wt. % of ceramide, 2 wt. % of cetares-4 and 3 wt. % of cholesterol were mixed and homogenized. The mixture of 3 wt. % of 2-O-beta-fructosyl-L-ascorbic acid, 0.4 wt. % of dicetylphosphate, 5.0 wt. % of conc-glycerin, 22 wt. % of sunflower oil, 0.5 wt. % of carboxyvinylpolymer, and preservatives was dissolved by heating in accordance with well-known procedure in the art. 56.5 wt % of distilled water was added thereto and emulsified by emulsifier. Appropriate amount of flavoring agent was added thereto, mixed to obtain purposed nutrient cream. The cream can be used as a sun block, skin beauty and skin whitening agent with high quality.

Preparation Example 5

Massage Cream 0.2 wt. % of carboxyvinylpolymer, 5 wt. % of glycerin, 3 wt. % of butylenes glycol, 3 wt % of propylene glycol, 22.3 wt. % of distilled water, and miscellaneous preservatives were mixed with heating at 80-85° C. and poured to emulsifier apparatus. 10 wt. % of wax, 1.5 wt. % of polysorbate 60, 0.8 wt. % of sorbitane sequiolate, 40 wt % of liquid paraffin, 5.0 wt. % of squalene, 4 wt. % of caprylic/capric triglyceride and 0.2 wt. % of triethanolamine were mixed with heating at 80-85° C. and poured to emulsifier apparatus. After the end of emulsification, the mixture was mixed and cooled at 50° C. Coloring agent was poured thereto, cooled at 45° C. and flavoring agent was added thereto and cooled at 35° C. 5 wt. % of 2-O-beta-fructosyl-L-ascorbic acid was added thereto and mixed to obtain purposed massage cream. The cream can be used as a sun block, skin beauty and skin whitening agent with high quality.

Preparation Example 6

Nutrient Essence 1.7 wt. % of sitosterol, 1.5 wt. % of polyglyceryl 2-olate, 0.7 wt. % of ceramide, 1.2 wt. % of cetares-4 and 1.5 wt. % of cholesterol were mixed and homogenized. The mixture of 5 wt. % of 2-O-beta-fructosyl-L-ascorbic acid, 0.4 wt. % of dicetylphosphate, 5.0 wt. % of conc-glycerin, 15 wt. % of sunflower oil, 0.2 wt. % of carboxyvinylpolymer, 0.2 wt. % of xantan gum and preservatives was dissolved by heating in accordance with well-known procedure in the art. 67.6 wt % of distilled water was added thereto and emulsified by emulsifier. Appropriate amount of flavoring agent was added thereto, mixed to obtain purposed nutrient essence. The essence can be used as a sun block, skin beauty and skin whitening agent with high quality.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, present invention provides novel cosmetic composition comprising beta-fructosyl-L-ascorbic acid derivatives produced by fructose transfer reaction from ascorbic acidskin whitening cosmetic composition as an cream, skin, lotion, pack and the like.

The invention claimed is:

1. A cosmetic composition comprising chemically stable novel β-fructosyl-L-ascorbic acid derivatives represented by general structural formula (I) produced by fructose conversion reaction from ascorbic acid:

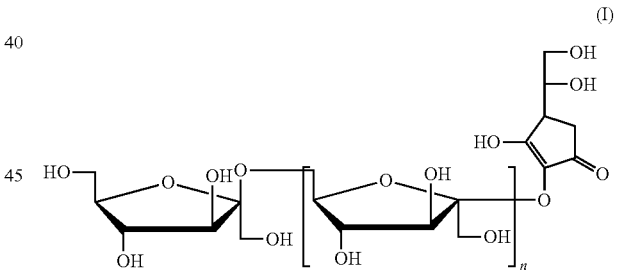

Wherein n is integer of 0 to 10.

2. The cosmetic composition of claim 1, wherein said derivative is 2-O-β-fructosyl-L-ascorbic acid.

3. The cosmetic composition of claim 1, wherein said cosmetic composition comprises 0.001 to 40 w/w % of compound as set forth in claim 1.

4. The cosmetic composition of claim 1, wherein said cosmetic composition is selected from the group consisting of astringent, nutrient lotion, nutrient cream, massage cream, essence, pack, foundation, cleansing water, soap, treatment and beauty solution.

* * * * *